(12) United States Patent
Albertini et al.

(10) Patent No.: US 6,865,925 B2
(45) Date of Patent: Mar. 15, 2005

(54) COLLISION TEST APPARATUS

(75) Inventors: Carlo Albertini, Ispra (IT); Kamel Labibes, Orino (IT); George Solomos, Casciago (IT)

(73) Assignee: European Community, Luxembourg (LU)

( * ) Notice: Subject to any disclaimer, the term of this patent is extended or adjusted under 35 U.S.C. 154(b) by 0 days.

(21) Appl. No.: 10/203,900

(22) PCT Filed: Jun. 27, 2001

(86) PCT No.: PCT/IB01/01141
§ 371 (c)(1),
(2), (4) Date: Aug. 15, 2002

(87) PCT Pub. No.: WO02/01185
PCT Pub. Date: Jan. 3, 2002

(65) Prior Publication Data
US 2003/0074949 A1 Apr. 24, 2003

(30) Foreign Application Priority Data
Jun. 30, 2000 (GB) .............................. 0015940

(51) Int. Cl.$^7$ ................................................ G01M 7/00
(52) U.S. Cl. ........................................................ 73/12.09
(58) Field of Search ........................... 73/12.01, 12.04, 73/12.08, 12.09

(56) References Cited

U.S. PATENT DOCUMENTS 5,018,113 A * 5/1991 Strange et al. .............. 367/127
5,154,080 A * 10/1992 Hill et al. ..................... 73/597
5,261,505 A * 11/1993 Holroyd et al. ............. 180/274

* cited by examiner

Primary Examiner—Max Noori
(74) Attorney, Agent, or Firm—Pillsbury Winthrop LLP

(57) ABSTRACT

A collision test apparatus having input and output members formed from incompressible liquids and between which is positioned a sample whose impact characteristics are to be measured. A compression wave is input to the input member and propagated through the sample and in the output member. Suitable detectors detect the input compression wave, output compression wave and any pan of the input compression wave reflected off the sample.

14 Claims, 5 Drawing Sheets

COLLISION TEST APPARATUS

CROSS REFERENCE TO RELATED APPLICATIONS

This application is a national phase application based on PCT/IB01/01141, filed Jun. 27, 2001, and which further claims priority from British Application No. 0015940.0, filed Jun. 30, 2000. These applications in their entirety are incorporated herein by reference.

This invention relates to a collision test apparatus and more particularly to such an apparatus for testing impact characteristics of human body parts with structural vehicle parts in collisions.

It has been proposed to measure impact characteristics of human body parts in vehicle collisions using collision test apparatus formed from a modification of a so-called Hopkinson bar. A Hopkinson bar is a well known device for measuring the mechanical properties of materials under impact loading.

Such apparatus usually comprises a projectile which impacts against an impact bar. The impact of the projectile with the input bar causes a compression incident pulse $\epsilon_I$ to be generated in the input bar which propagates through the input bar. A specimen to be measured is positioned between the input bar and an output bar and when the incident pulse $\epsilon_I$ reaches the interface between the input bar and the specimen, a part of the incident pulse is reflected $\epsilon_R$ and the other part $\epsilon_T$ propagates into the specimen where it deforms the specimen and then propagates into the output bar. By positioning strain gauges on the input bar and output bar respectively, $\epsilon_I$ and $\epsilon_R$ can be measured as can $\epsilon_T$. Measurement of $\epsilon_I$, $\epsilon_R$ and $\epsilon_T$ allows the calculation of mechanical properties (stress $\sigma$, strain $\epsilon$, strain rate $\dot\epsilon$) of the specimen by application of the uniaxial elastic wave propagation theory:

$$\sigma_s = E\frac{A_o}{A_s}\varepsilon_T,$$

$$\varepsilon_s = \frac{2C_o}{L_s}\int_{ox}^{t}\varepsilon_R dt$$

$$\dot\varepsilon_s = \frac{2C_o}{L_s}\varepsilon_R$$

where
- $E$ = elastic modulus of the bar
- $A_o$ = cross sectional area of the bar
- $A_s$ = cross sectional area of the specimen
- $C_o$ = elastic wave speed in the bar
- $L_S$ = specimen gauge length
- $t$ = time However, the uniaxial elastic wave propagation theory can only be correctly used if the cross section of the input and output bars is higher than the cross section of the specimen and the respective bars must remain elastic as the specimen deforms until fracture. Furthermore, the diameter of the input and output bars must be much smaller than the wavelength of $\epsilon_I$. Still further there must not be a large mechanical impedance mismatch between input and output bars and the specimen. Therefore the mechanical impedance of the bar $Z=\rho_{BAR}{}^*C_{BAR}{}^*A_{BAR}$ cannot be an order of magnitude higher than the mechanical impedance of the specimen $z_{SPEC}=\rho_{SPEC}{}^*C_{SPEC}{}^*A_{SPEC}$ where $\rho$=material density
A=cross sectional area
C=sound speed In fact, if the mechanical Impedance mismatch is higher than an order of magnitude there is nearly total reflection of $\epsilon_I$ at the interface between input bar and specimen and $\epsilon_T$ will be so small that it cannot be recorded with accuracy in the output bar.

The consequences of mechanical impedance mismatch have hitherto limited practically the application of collision test apparatus formed in this way to the testing of specimens of steel, concrete or medium density (3–4 g/mm$^3$) composite materials. In particular this type of apparatus has not been capable of being used to measure impact characteristics of human soft tissue or other soft materials or bodies which stimulate such tissue.

It is accordingly an object of the present invention to provide a collision test apparatus in which a modified Hopkinson bar system can be used to measure the impact characteristics of soft tissue or other soft materials and in which the problems associated with impedance mismatch mentioned above are obviated.

Thus and in accordance with a first aspect of the present invention therefore there is provided a collision test apparatus comprising an input member and output member between which a specimen to be measured can be positioned, said input member being adapted to receive an input compression wave and propagate the same to the sample and said output member being adapted to receive an output compression wave from said sample and detection means to detect the input compression wave, the output compression wave and any part of said input compression wave reflected from said sample wherein said input and output members comprise incompressible liquids.

With this arrangement it is possible to provide collision test apparatus in which the impact characteristics of human tissue or other soft materials can be measured since the mechanical impedance mismatch is reduced to less than an order of magnitude by the use of incompressible liquids in the input and output members.

In accordance with a second aspect of the present invention there is provided a method of testing impact characteristics of a material comprising interposing a sample whose characteristics are to be measured between input and output members each comprising incompressible liquids, arranging for an input compression wave to be created in the input member and propagated to the sample, detecting the input compression wavy, any output compression wave in the output member and any part of the input compression wave reflected from the sample.

The invention will now be described further by way of example only and with reference to the accompanying drawings in which.

Figure 1:
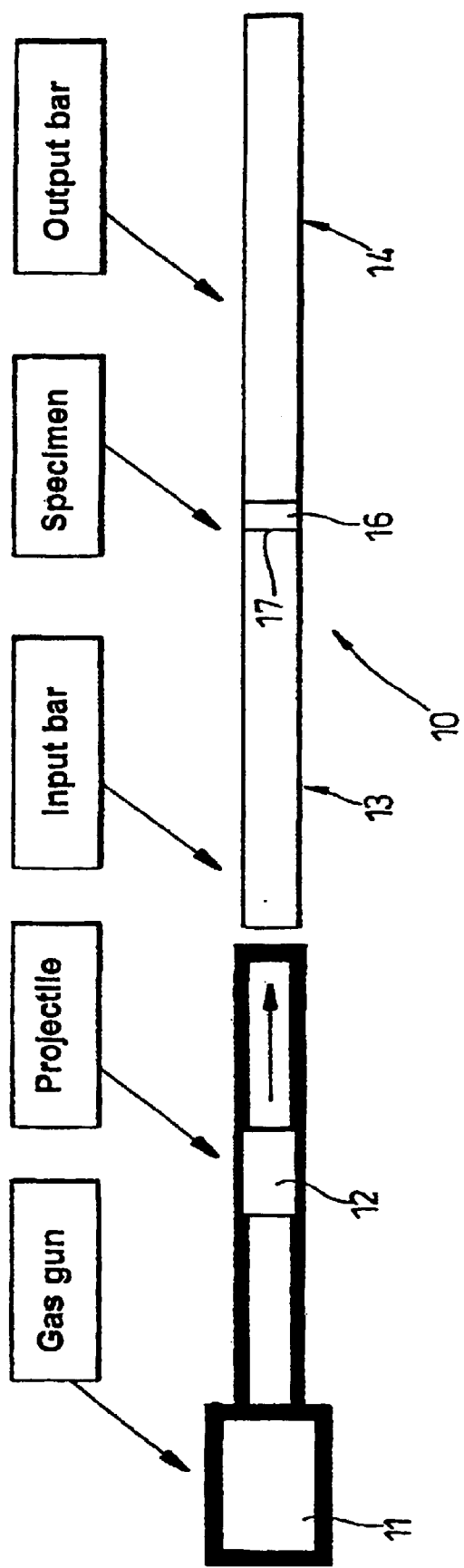
FIG. 1 shows a schematic representation of a known form of collision test apparatus utilising a Hopkinson bar.

Referring now to the drawings, there is shown in FIG. 1, a known form of collision test apparatus 10 incorporating a Hopkinson bar arrangement.

The apparatus 10 comprises a gas gun 11 which fires a projectile 12 at high speed at an input bar 13. The input bar 13 is linked to an output bar 14 and a specimen 16, whose characteristics are to be measured, is sandwiched between the input and output bar 13, 14 respectively.

In use, the projectile 12 is fired at high speed at the input bar 13 and upon impact creates a compression wave $\epsilon_I$ in the input bar 13 which travels along the input bar 13 to the interface 17 between the input bar 13 and the specimen 16. As previously explained, at this Interface 17, a part of the wave is reflected $\epsilon_R$ dependent on the specimen deformation and on the impedance mismatch between the bar 13 and the specimen 16 and the remaining part $\epsilon_T$ is transmitted into the specimen 16 and deforms the specimen 16. The transmitted wave $\epsilon_T$ then exits the specimen 16 and is transmitted into the output bar 14. $\epsilon_I$, $\epsilon_R$ and $\epsilon_T$ are conveniently measured using strain gauges (not shown) mounted on the input and output bars 13, 14 respectively and, from the values measured by the strain gauges, the impact characteristics of the specimen can be calculated using the equation set out in the introductory paragraphs of the specification.

The problem with this arrangement is that it cannot be used to measure the properties of a specimen which has a difference in mechanical impedance which is greater than 1 magnitude mismatched with the mechanical impedance of the input or output bar 13 or 14 such as, for example would be the case with human tissue or other soft material since $\epsilon_R$ would tend towards 100% and $\epsilon_T$ would be almost zero with the consequence of a low accuracy in the measurement of $\epsilon_T$ and therefore low accuracy in the measurement of the strength of the specimen.

Figure 2:
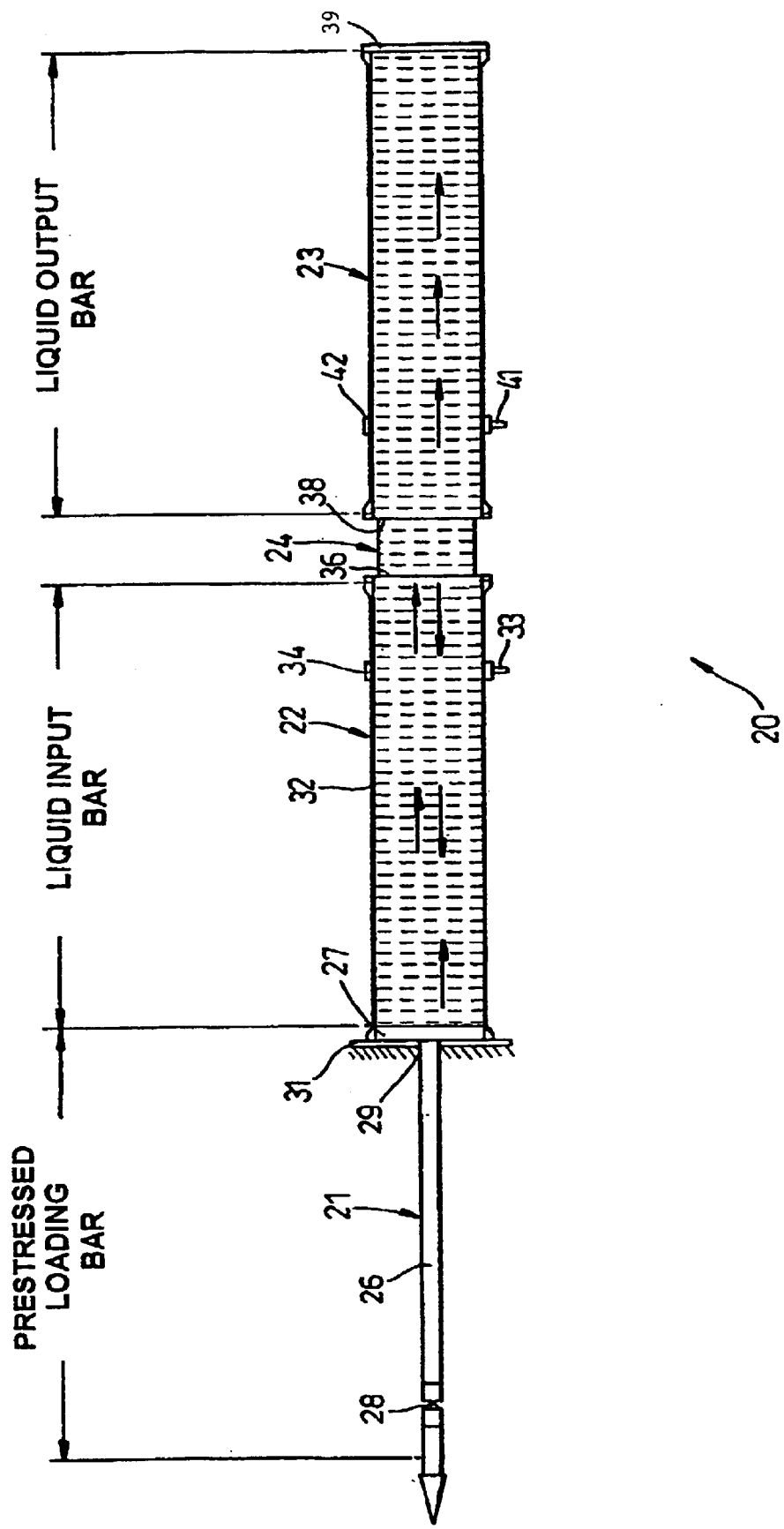
FIG. 2 shows in schematic form a first embodiment of collision test apparatus according to the present invention.

A first embodiment of apparatus 20 according to the invention is shown in FIG. 2.

The apparatus 20 comprises a prestressed loading member 21 which extends into a liquid input member 22 which is linked to a liquid output member 23 by a specimen 24.

The prestressed loading member 21 comprises a plunger arrangement formed by a plunger member 26 and a plunger plate 27. The plunger member 26 is provided with an area of weakness 28. The area of weakness 28 may comprise a portion of reduced diameter or any other suitable configuration which leads to a reduction in the tensile strength in the region of the area 28. The plunger member 26 extends into one end of the liquid input member 22 through an aperture 29 in an input closure 31 such that the plunger plate 27 is provided within the liquid input member 22 and plunger member is adapted for connection to a tensioning device (not shown).

The input closure 31 is rigidly connected to ground and acts to support the plunger plate 97 in the liquid when the plunger is placed under tension by the tensioning device.

The liquid input member 22 comprises a hollow cylindrical member 32 containing a non incompressible liquid and which is preferably formed from steel or aluminium. One end of the input member 22 is closed off by the input closure 31 through which the plunger arrangement extends. At least one piezo electric transducer 33 extends through the wall of the hollow cylindrical member 32, into the interior thereof to measure pressure changes in the liquid and the transducer is disposed at an appropriate distance from the opposite end of the member 22 to the input closure 31. At least one strain gauge 34 is also provided on the wall of the hollow cylindrical member 32 also at an appropriate distance from the opposite end of the input member 22, and the strain gauge 34 acts to measure deformation of the circumferential wall of the liquid input member 22 due to pressure changes in the liquid therein. The distance of the piezo-transducer 33 or strain gauge 34 from the interface between input member 22 and specimen 24 must be sufficient for recording separately the incident pulses and the reflected pulses (e.g. 0.5 m). The opposite end of the liquid input 22 member is closed off by a seal 36 in the form of a soft membrane.

The liquid output member 23 is generally similar to the input member 22 and an end thereof closest to the input member 23 is also closed off by a seal 38 in the form of a soft membrane and the other end is closed off by an output closure 39. Likewise at least one piezo electric transducer 41 and at least one strain gauge 42 are provided adjacent to one end at the same distance from the interface between the output member 23 and specimen 24 in a manner similar to that described above in relation to the liquid input bar 22.

The incompressible liquid which is provided in the input and output members 22, 23 is chosen such that the difference in mechanical impedance between the input member 22 and output member 23 with respect to the specimen 24 whose properties are to be measured is defined as follows:

$$1 < \frac{A_{Li}\rho_{Li}C_{Li}}{A_{spec}\rho_{spec}C_{spec}} < 10$$

where $A_{Li}$=cross sectional area of the liquid of input ends output member $\rho_{Li}$=liquid density of input or output member $C_{Li}$=speed of sound in the liquid $A_{spec}$, $\rho_{spec}$, $C_{spec}$ are the same values for the specimen.

Normally it would be simple to achieve this result by arrangement of $$\frac{A_{Li}}{A_{spec}} < 10 \: since \frac{\rho_{Li}}{\rho_{spec}} \: and \: \frac{C_{li}}{C_{spec}} \underline{N} 1$$

In use, a soft specimen 24 whose characteristics are to be measured is placed between the input and the output member 22 and 23 and is held between the soft seals 36 and 38 which close off ends of the input and output members 22, 23 respectively. The prestressed loading member 21 is tensioned in any suitable manner until the plunger member 26 fractures in the region of the area of weakness 28. This causes the elastic potential energy stored in the plunger member 26 to be released as a member 26 is driven towards the input member 22 which means that the plunger plate 27 moves within the hollow input member 22 and causes the generation of a longitudinal compression wave pulse $P_I$ in the liquid in the input member 22. The compression pulse propagates through the input member 22 until it passes through the seal 36 and meets the soft sample 24. When the compression pulse meets the soft sample 24, due to the deformation of the specimen 24, a part of the compression wave is reflected $P_R$ and another part $P_T$ is transmitted into the soft sample 24 to deform the sample. The transmitted part $P_T$ passes through the sample 24 and passes into the output member 23. Furthermore, the use of a incompressible liquid in the input and output members 22, 23 means that the pressure changes in the input and output members due to the generation of the longitudinal compression wave pulses will be transmitted with the same values to the wall of the respective member 22, 23. This means that the strain gauges 34, 41 on the input and output members 22, 23 can record the circumferential deformation of the wall $\epsilon_{CI}$, $\epsilon_{CR}$, $\epsilon_{CT}$ of the input and output members 22, 23 caused respectively by the incident pressure pulses in the liquid $P_I$, $P_R$ and $P_T$ as function of time and as a result can calculate the pressure values $P_I$, $P_R$ and $P_T$.

In fact the pressure P inside the liquid in each member is related to the circumferential deformation of the wall of the members, which the strain $$\varepsilon_{circum^*} = \frac{PR}{ED}$$

gauge measures, as follows:
Where P=pressure in liquid
R=radius of hollow cylindrical member
E=elastic modulus of hollow cylindrical member material
D=hollow cylindrical member wall thickness
Therefore the value of $P_I$, $P_R$ and $P_T$ can be calculated from the following relationships $$P_1 = \frac{\varepsilon_{CI} \cdot D \cdot E}{R} \quad \text{where} \quad \varepsilon_{CI} = \text{circumferential deformation of the hollow cylindrical member caused by } P_1$$

$$P_R = \frac{\varepsilon_{CR} \cdot D \cdot E}{R} \quad \varepsilon_{CR} = \text{circumferential deformation of the hollow cylindrical member provoked by } P_R$$

$$P_T = \frac{\varepsilon_{CT} \cdot D \cdot E}{R} \quad \varepsilon_{CT} = \text{circumferential deformation of the hollow cylindrical member provoked by } P_T$$

The values $P_I$, $P_R$ and $P_T$ i.e. the liquid pressure values can alternatively or additionally be directly measured by the piezo electric devices 33, 41 mounted on the input and output members 22, 23 respectively.

Once the values of $P_I$, $P_R$ and $P_T$ as a function of time have been calculated or directly measured, the mechanical properties of the soft sample, such is the stress, strain and strain rate therein caused by the impact can be calculated using the following equations:

$$\frac{\sigma(t)}{ST} = \frac{A_{LIQUID} p_T(t)}{A_{ST}}$$

$$\frac{\varepsilon(t)}{ST} = \frac{2}{L_{ST}} \int_0^t V_R(t) dt$$

$$\frac{\dot{\varepsilon}(t)}{ST} = \frac{2}{L_{ST}} V_R(t)$$

$$V_R(t) = \frac{P_R(t)}{\rho_{LIQ} C_{LIQ}}$$

Where:
$\sigma_{ST}$=stress in the soft tissue
$\varepsilon_{ST}$=strain of the soft tissue
$\dot{\varepsilon}_{ST}$=strain rate of the soft tissue
$A_{LIQUID}$=cross sectional area of the liquid column
$A_{ST}$=cross sectional area of the tissue specimen
t=time
$C_{LIQ}$=wave velocity in the liquid
$L_{ST}$=gauge length of the soft tissue specimen
$V_R$=liquid particle velocity correlated with the reflected pressure pulse PR.

The values $\sigma_{ST}$, $\varepsilon_{ST}$ and $\dot{\varepsilon}_{ST}(t)$ are values which indicate how the soft sample will react upon an impact.

It is envisaged that it should be possible to place a human soft tissue sample 24 between the input and output members 22, 23 and the characteristics of this tissue can be measured directly using the apparatus of the invention. This would not be possible with existing arrangements which employ solid input and output members since the mechanical impedance mismatch would result in the impossibility of recording $P_I$, $P_R$ and $P_T$.

Figure 3:
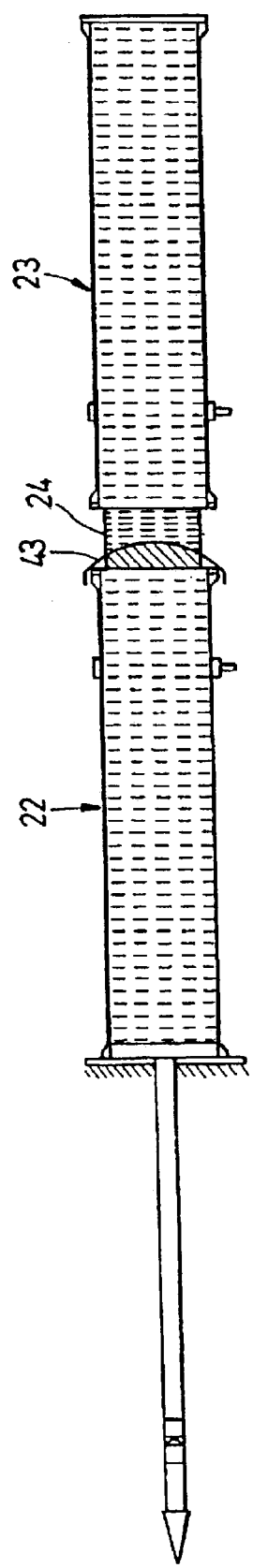
FIG. 3 shows in schematic form a second embodiment of collision test apparatus according to the present invention.
Figure 4:
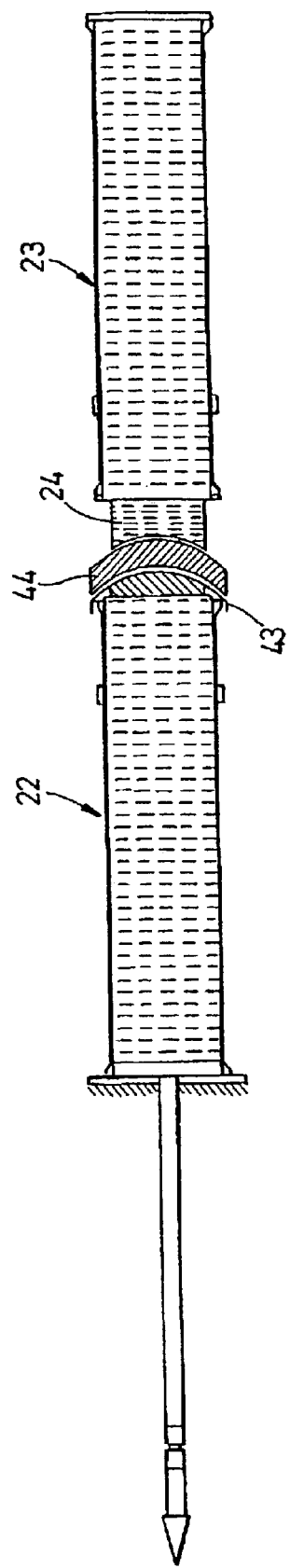
FIG. 4 shows in schematic form a third embodiment of collision test apparatus according to the present invention.

As an alternative to measuring the characteristics of the soft tissue sample directly, as shown in FIG. 3, an automobile structural part 43 can be placed in contact with the sample 24 between the input and output members 22, 23 and using this arrangement it is possible to quantify the injuries consequence of a collision of this structural part on the tissue. Still further, as shown in FIG. 4, the effect of impact energy absorption materials 44 on the reduction of the injuries sustained by a human tissue sample 24 can be examined by placing the material between the automobile part 43 and the tissue sample 24.

Figure 5:
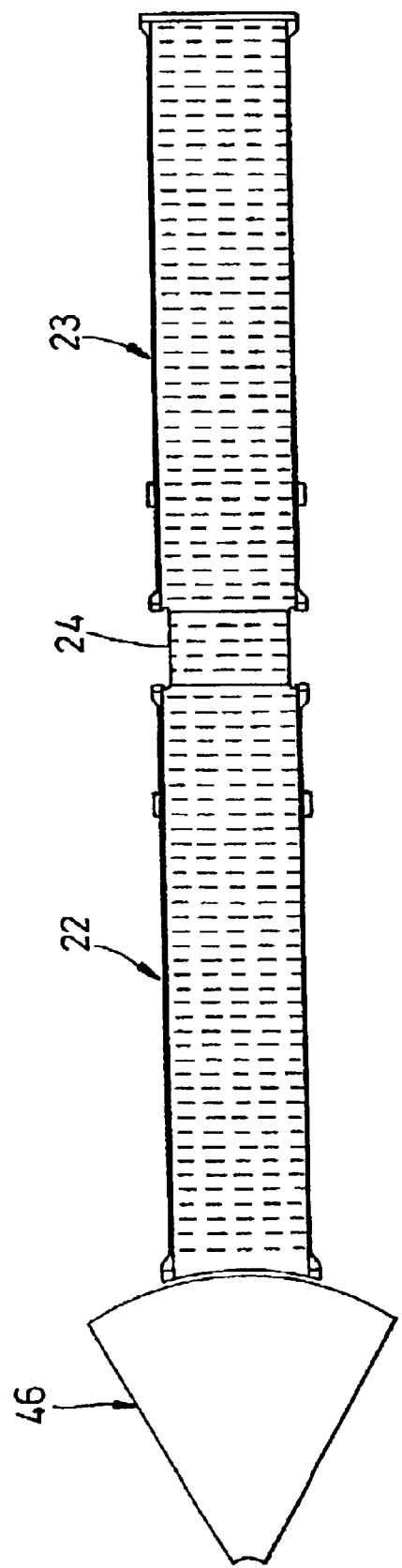
FIG. 5 shows in schematic form a fourth embodiment of collision test apparatus according to the present invention.

As a still further alternative, as shown in FIG. 5, it is possible to, rather than use a prestressed loading bar, activate an automobile airbag arrangement 46 indirectly in front of the liquid input member 22. The activation of the airbag arrangement 46 will result in the generation of a compression pulse in like manner to that generated by the use of a prestressed loading bar and accordingly, the incident compression $P_I$, reflected compression wave $P_R$ and transmitted pressure wave $P_T$ having measured as described above. Accordingly the effects of the compression wave pulse on the human tissue sample 24 can be measured.

It is of course to be understood that the invention is not intended to be restricted to the details of the above embodiments which are described by way of example only.

What is claimed is:

1. A collision test apparatus comprising an input member and an output member between which a sample to be measured can be positioned, said input member being adapted to receive an input compression wave and propagate the same to the sample and said output member being adapted to receive an output compression wave from said sample and detection means to detect the input compression wave, the output compression wave and any pan of said input compression wave reflected from said sample wherein said input and output members comprise incompressible liquids.

2. Apparatus according to claim 1, wherein the mechanical impedance of the liquid is less than one order of magnitude difference from that of the sample and the relationship between the respective mechanical impedances is defined by the following equation $$1 < \frac{\rho_{LIQ}^* C_{LIQ}^{*A} B_{AR\,LIQ}}{\rho_{SAMPLE}^* C_{SAMPLE}^* A_{SAMPLE}} > 10$$

where $\rho$=density, C=elastic wave speed and A=cross-section area.

3. Apparatus according to claim 2, wherein the liquid is chosen so that $P_{LIQ}=\rho_{SAMPLE}$ and $C_{LIQ}=C_{SAMPLE}$ whereby the following equation defines the relationship $$1 < \frac{A_{LIQ}}{A_{SAMPLE}} < 10$$

4. Apparatus according to claim 1, wherein said input and output members comprise hollow cylindrical members, ends of which are in contact with said sample and being adapted so as to have a density substantially equal to that of the sample.

5. Apparatus according to claim 4, wherein the adaptation of the ends comprise closure members which close off the end of the respective input and output members.

6. Apparatus according to claim 1, wherein at least one strain gauge is mounted adjacent each of the input and output members to measure circumferential deformation $\varepsilon_{CIRCUMF}$ of a said me during testing whereby the pressure in each member can be calculated according to the following equation:

$$\varepsilon_{CIRCUMF} = \frac{PR}{tE}$$

where R=member radius, E=elastic modulus of member material and T=member wall thickness which is directly proportional to pressure pulse amplitude $P_R$ or $P_T$ in the respective member.

7. Apparatus according to claim 1, wherein the amplitude of the pressure pulse is measured by a pressure transducer in contact with the liquid of the input and output member.

8. Apparatus according to claim 1, wherein the diameter D of the input member and output member is at least a factor of 10 smaller than the wavelength of the generated incident pressure pulse $P_I$ such that whereby the stress $\sigma_{ST}$, $\epsilon_{ST}$ and the strain rate $\epsilon_{ST}$ of the sample can be calculated upon measurement of an incident pressure pulse $P_I$ and a reflected pressure pulse $P_R$ in the input member and a transmitted pressure pulse $P_T$ in the output member according to the following equations:

$$\frac{\sigma(t)}{ST} = \frac{A_{LIQUID}P_T(t)}{A_{ST}}$$

$$\frac{\varepsilon(t)}{ST} = \frac{2}{L_{ST}} \int_0^t V_R(t)dt$$

$$\frac{\varepsilon(t)}{ST} = \frac{2}{L_{ST}} V_R(t)$$

$$V_R(t) = \frac{P_R(t)}{\rho_{LIQ}C_{LIQ}}$$

Where:
$\sigma_{ST}$=stress in the soft tissue
$\epsilon_{ST}$=strain of the soft tissue
$\epsilon_{ST}$=strain rule of the soft tissue
$A_{LIQUID}$=cross sectional area of the liquid column
$A_{ST}$=cross sectional area of the tissue specimen
t=time
$C_{LIQ}$=wave velocity in the liquid
$L_{ST}$=gauge length soft tissue specimen
$V_K$=liquid particle velocity correlated with the reflected pressure pulse PR.

9. Apparatus according to claim 1, wherein the apparatus further includes an impact mitigation material provided interposed between said sample and said input member.

10. Apparatus according to claim 1, wherein the input compression wave is generated in the input member by inflation of an inflatable impact mitigation device.

11. A method of testing impact characteristics of a material comprising interposing a sample whose characteristics are to be measured between input and output members each comprising incompressible liquids, arranging for an input compression wave to be created in the input member and propagated to the sample, detecting the input compression wave, any output compression wave in the output member and any pant of the input compression wave reflected from the sample.

12. A method according to claim 11 further including the step of interposing between said sample and said input member, an impact mitigation material.

13. A method according of claim 11 or claim 12, wherein the step of arranging for an input compression wave to be created in said input member is carried out by inflation of an inflatable impact mitigation device.

14. A method according to claim 11, wherein said input and output members comprise hollow cylindrical members, and wherein the incident pressure pulse $P_I$ reflected $P_R$ and transmitted $P_T$ along the axis of said members are determined from measurement of pressure exerted in the radial direction performed by strain gauges bonded on said members or by pressure transducers mounted on said members and in contact with the liquid.

* * * * *

UNITED STATES PATENT AND TRADEMARK OFFICE
CERTIFICATE OF CORRECTION

PATENT NO. : 6,865,925 B2
DATED : March 15, 2005
INVENTOR(S) : Carlo Albertini et al.

It is certified that error appears in the above-identified patent and that said Letters Patent is hereby corrected as shown below:

Title page,
Item [56], References Cited, U.S. PATENT DOCUMENTS, add the following:
-- 6,109,093     *     08/2000     Albertini et al. …..73/12.08 --.
Add the following:
-- FOREIGN PATENT DOCUMENTS
1065492 A2    01/2001     European Pat. Off.
1065492 A3    01/2004     European Pat. Off. --.
Item [57], ABSTRACT,
Line 5, replace "in" with -- into --.
Line 7, replace "pan" with -- part --.

Signed and Sealed this

Fourth Day of October, 2005

JON W. DUDAS
*Director of the United States Patent and Trademark Office*